(12) United States Patent
Whiteley

(10) Patent No.: US 8,343,903 B2
(45) Date of Patent: Jan. 1, 2013

(54) BIOSTATIC MEDICAL CLEANING PRODUCTS

(75) Inventor: Reginald Keith Whiteley, New South Wales (AU)

(73) Assignee: Whiteley Holdings Pty Ltd, Sydney, New South Wales (AU)

( * ) Notice: Subject to any disclaimer, the term of this patent is extended or adjusted under 35 U.S.C. 154(b) by 443 days.

(21) Appl. No.: 12/503,900

(22) Filed: Jul. 16, 2009

(65) Prior Publication Data

US 2010/0029530 A1  Feb. 4, 2010

(30) Foreign Application Priority Data

Jul. 30, 2008 (AU) ................................ 2008903887

(51) Int. Cl.
*C11D 1/72* (2006.01)
*C11D 1/835* (2006.01)
*C11D 3/26* (2006.01)
*C11D 3/43* (2006.01)

(52) U.S. Cl. ........ 510/161; 510/238; 510/245; 510/255; 510/259; 510/264; 510/272; 510/423; 510/433; 510/434; 510/435; 510/470; 510/477; 510/488; 510/492; 510/499; 510/504; 510/505; 510/506

(58) Field of Classification Search .................. 510/161, 510/238, 245, 255, 259, 264, 272, 423, 433, 510/434, 435, 470, 477, 488, 492, 499, 504, 510/505, 506; 134/2, 41
See application file for complete search history.

(56) References Cited

U.S. PATENT DOCUMENTS

| | | | | |
|---|---|---|---|---|
| 3,699,047 A | * | 10/1972 | Petrey, Jr. ..................... 252/175 |
| 4,416,793 A | * | 11/1983 | Barrat et al. .................. 510/335 |
| 4,446,035 A | * | 5/1984 | Barrat et al. .................. 510/335 |
| 4,595,517 A | * | 6/1986 | Abadi ............................ 510/253 |
| 5,470,500 A | * | 11/1995 | Lupyan et al. ................ 510/394 |
| 5,714,453 A | * | 2/1998 | Neumiller ..................... 510/405 |
| 5,750,197 A | | 5/1998 | van Ooij et al. |
| 6,261,638 B1 | | 7/2001 | van Ooij et al. |
| 6,387,871 B2 | | 5/2002 | Faber |
| 6,395,698 B1 | | 5/2002 | Daun et al. |
| 6,489,285 B2 | | 12/2002 | Faber |
| 7,001,873 B2 | | 2/2006 | McDonnell et al. |
| 2002/0173437 A1 | | 11/2002 | Rabon et al. |
| 2010/0206328 A1 | * | 8/2010 | Dreilinger et al. ................ 134/6 |

FOREIGN PATENT DOCUMENTS

| WO | WO98/19536 | * | 5/1998 |
| WO | WO 98/19536 A1 | | 5/1998 |
| WO | WO02/07789 | * | 1/2002 |
| WO | WO 02/07789 A1 | | 1/2002 |

* cited by examiner

*Primary Examiner* — Gregory Delcotto
(74) *Attorney, Agent, or Firm* — Andrew S. Langsam; Pryor Cashman LLP

(57) ABSTRACT

There is disclosed a cleaning composition comprising (i) 0.1 to 10 percent by weight of the cleaning composition of a biofilm removing detergent solution comprising a combination of an alkyl (C8-18) polysaccharide, a non-ionic surfactant and a nitrogen containing surfactant-biocide (ii) 2 to 80 percent by weight of the cleaning composition of one or more polar solvent (iii) 0.5 to 15 percent by weight of the cleaning composition of one or more primary amine (iv) two or more chelating agents (v) 0.1 to 5.0 percent by weight of the cleaning composition of an alkaline buffer system providing a pH of about 11.5 to 13.3 in aqueous solution (vi) 0.005 to 5.0 percent by weight of the cleaning composition of an alkoxyaminosilane. Also disclosed is a process of cleaning, decontaminating and/or passivating metallic surgical instruments and/or equipment using the composition of the invention.

20 Claims, No Drawings

BIOSTATIC MEDICAL CLEANING PRODUCTS

Cleaning of surgical instruments soiled with biological residues contaminated with prions remains among the last challenges of medical disinfection. This is becoming an increasing problem with the progressive spread of slow developing fatal diseases emanating from the unique infective proteins called prions; commonly referred to as Mad Cow Disease or Creutzfeldt-Jacob Disease, after its discoverer.

Technically, the disease is known as Transmissible Spongiform Encephalopathy (TSE); and found in nature in humans and animals and found in consequence thereof as a contaminant of floors, work surfaces, instruments, storage facilities, food processing equipment and other handling equipment, in pharmaceutical preparations and veterinary institutions.

The chemical nature of these unique and distinctive proteins has been the subject of extensive research, the key literature of which is described within the context of this invention in a recent paper by Graham S Jackson et al: *An enzyme-detergent method of effective prion decontamination of surgical stainless steel*; Journal of General Virology, (2005), 86, 869-878. This paper describes the recent approach to the decontamination of stainless steel instruments employed in surgery where prions are likely to be present as residues on the surface of used instruments. Interestingly, these proteins have a particular affinity (reactivity) to stainless steel and like alloys to which they bind in a quite chemical resistant manner.

Recent research has identified quite a number of variants of the original TSE prion, each variant having distinctive reactivity and response to methods of chemical decontamination.

The particularly unique property of prions is that they must be destroyed chemically by major structural modification before infectivity is lost. Normal and current practices for reprocessing used stainless steel instruments are ineffective. Extreme measures such as immersion in strong sodium hydroxide solutions or acid descaleing of metal surfaces are required to guarantee loss of infectivity by partial or preferably total destruction of the proteins involved. Products and processes thus far evaluated for routine instrument decontamination cannot yet to be totally effective in stopping transmission of infective prions from passing on to successive patients.

The most interesting recent patent U.S. Pat. No. 7,001,873 to McDonald et al employs a system of detergent pre-cleaning using conventional detergents followed by exposure to the very strong oxidizing agent, peracetic acid, at temperatures from 55 to 60° Celsius. The detergent relies heavily upon the use of strong alkali, either sodium or potassium hydroxide, to partially unfold the coiling of the prion proteins permitting the oxidizing agent to attach the residue of the protein. This has not yielded total loss of infectivity in reported simulated research despite current promotion of the system commercially.

A recent overview of the problem of preventing the spread of prion diseases is that by J. Stephenson: Journal of Hospital Hygiene (2007) 65 (52) 14-18. This definitive article makes it quite clear that developing satisfactory practically applicable totally effective methods of prion decontamination is still very much work in progress. There is not as yet a simple, economical and efficient prion destruction method, nor an assured method of evaluating prion decontamination available from research or commercial practice; saving inserting fine stainless steel wire into the brain of rats and noting onset of disease symptoms.

Some of the reasons for chemical resistance of prions, including their chemistry, is discussed within the context of this invention in USP 20040106188 submitted by Ktitzler, et al. This embodies the use of several enzymes in association with typical surfactants and detergent components; and relies on the effectiveness of the enzyme preparations to destroy all soil and prion material on surfaces. It has not been found acceptable as a practical method under independent testing and has therefore no practical significance.

In a most recent study specifically evaluating recently available enzymes intended primarily to assist decontamination of surface-bound human-derived prions, (V A Lawson et al, J. General Virology, (2007), 88, 2906-2914), the conclusion read "The RMEC formulations are non-corrosive, neutral in pH detergents that have been developed for the cleaning of endoscopes. Therefore, the protocols described can be used for the routine cleaning of surgical instruments without the corrosive effects associated with NaOH (McDonnel & Bourke, 2003) and may minimize the risk of prion disease transmission through general surgical procedures (Collins et al, 1999). It will be of importance to validate further the efficacies of these protocols against other human prion strains."

Clearly, while enzyme based detergents are useful they cannot be guaranteed to totally decontaminate human prions bound to the surface of surgical surfaces.

The emerging fact from the very large range of chemical methods so far evaluated for prion removal is that all fail to release the tightly bound protein residues from the surface of stainless steels and like alloys; due unquestionably to tenacious binding to stainless steels and other metals used for manufacture of surgical instruments.

Additionally, no serious attempt has been made to develop and evaluate the specific reactivities of the several variants of human prions thus far isolated. What has been found is by way of observation of results from infectivity testing and is therefore of general knowledge only.

Clearly literature reveals that different protein fractions so far studied, in particular PrP.sup.c and PvP.sup.Sc, (the latter believed to be the most infective to humans) have different reactivity and could account for the variation in tenacity binding of prions to surgical metals.

The significant factor is that totally effective cleaning and sterilizing of used surgical instruments in present generation automatic and semi-automatic Endoscope Reprocessing Machines (ERM's) is still not achieved routinely. Thus the inherent risk or disease transmission from prion diseases by nosocomial infection following surgery is still not eliminated in every day disinfecting practice.

These problems are seriously accentuated when biofilms are present on metallic surfaces where prions are found during surgery. Such prions, being located as reacted particles with metal ions on the surface of metallic instruments, are located beneath biofilm deposits. Until biofilms are removed quantitatively during processing residual prion proteins are assumed not accessible for decontamination procedures. In this regard it is important to note that no disinfecting protocol for medically derived prions has included the pre-step of forming a normal medical biofilm on metal surfaces before being subject to exposure to human derived prions prior to decontamination experiments. This is the medical reality of current routine surgical practice.

An important requirement is practical usefulness of chemical sterilants in existing processing equipment. Reliable cleaning and sterilizing processes desirably should be capable of effective use by semi-manual processes as well as use in low and high pressure endoscope reprocessing machines; of which a number of different designs are currently in use around the world: as well as being acceptable for use in existing continuous tunnel washing machines either single or dual stage batch washing equipment, including machinery already fitted with electronic concentration control devices.

As often occurs, strong chemicals (acidic and strongly alkali) employed in cleaning formulations have a tendency to leave freshly cleaned metallic surfaces in a semi-reactive state the result of which is promotion of oxidation colouring and subsequent corrosion of the surfaces of instruments and vessels of stainless steels—a very common and unrecognized problem leading to shortened acceptable life of very expensive equipment. It is therefore desirable that compounds capable of reacting with or dislodging prion-metallic complexes are also able to passivate or otherwise prevent corrosion of metals immediately after processing to avoid oxidation discolouration and discolouration.

A further very practical problem when instruments must be processed in hard water or mildly saline water is commonly found geographically on all major continents. Frequently, such classes of water must be employed in instrument reprocessing for reasons of either or both expense, lack of local resources or limited water availability.

It is common to find that water residues (salts) dried on freshly reprocessed metal surfaces lead to pitting corrosion of stainless, and related varieties of steels used in the manufacture of less expensive endoscopes. This is a truly major problem in hospitals and clinics in smaller towns and villages where facilities are relatively basic, but where prion diseases can be increasingly found. This is a further strong reason to be able to effectively passivate metals during reprocessing as well as endoscopes and other surgical equipment.

The above discussion of background art is included to explain the context of the present invention. It is not to be taken as an admission that any of the documents or other material referred to was published, known or part of the common general knowledge at the priority date of any one of the claims of this specification.

DESCRIPTION OF THE INVENTION

According to a first embodiment of the invention, there is provided a cleaning composition comprising:
(i) 0.1 to 10 percent by weight of the cleaning composition of a biofilm removing detergent solution comprising a combination of an alkyl (C 8-18) polysaccharide, a non-ionic surfactant and a nitrogen containing surfactant-biocide;
(ii) 2 to 80 percent by weight of the cleaning composition of one or more polar solvent selected from the group consisting of a primary or secondary alcohol, an ester, an ether, a ketone, a glycol, an aromatic alcohol and cyclic nitrogen solvent containing 8 or less carbon atoms;
(iii) 0.5 to 15 percent by weight of the cleaning composition of one or more primary amine selected from the group consisting of urea, methyl and ethyl urea, mono-di- and triethanolamine, aminomethane, alkylamines containing 1 to 4 carbon atoms, pyridine, paratoluidine, tetra (2-hydroxypropyl)ethylene diamine, an aromatic or cyclic amine containing 7 or less carbon atoms;
(iv) Two or more chelating agents selected from the group consisting of a substituted di and tri ethylamine, derivatives of phosphonic acid and its substituted derivatives, derivatives of nitrilotriacetic acid, derivatives of gluconic acid, glycine and derivatives thereof;
(v) 0.1 to 5.0 percent by weight of the cleaning composition of an alkaline buffer system providing a pH of about 11.5 to 13.3 in aqueous solution, comprising low molecular weight organic and/or hydroxyl organic acids containing 7 or less carbon atoms and a mono valent alkali;
(vi) 0.005 to 5.0 percent by weight of the cleaning composition of an alkoxyaminosilane.

According to a second embodiment of the invention, there is provided a process of cleaning, decontaminating and/or passivating metallic surgical instruments and/or equipment, by hand or machine processing, which process comprises applying to said instruments and/or equipment a cleaning composition according to the first embodiment.

According to a third embodiment of the invention, there is provided the use of a composition according to the first embodiment in diluted form in instrument washing and processing machines at temperatures from room temperature (20° C.) to 60° C., which machinery includes a water rinse cycle at the same temperature or hotter.

Previous patent specifications published by the author cover methods of formulating novel but very useful medical detergents and chemical sterilants. These are U.S. Pat. No. 6,525,101 covering non-aquoeus solutions of biocides and detergents; and U.S. Pat. No. 6,855,678 covering chemical biofilm removers, products derived from which are in current commercial and medical practice. Both of these two patents are incorporated herein by reference.

Research conducted since lodging these latter specifications has shown that while the means of proof of efficacy are still being debated it has become clear that all current chemical sterilants and detergents used as pre-cleaning solutions fail to recognize and attack the fundamental cause of chemical resistance of some variants of prions.

What constitutes the undeniable reason for more extreme chemical resistance is a combination of the precise nature of the ionically bound metal-prion complexes unique to the composition and spatial structure thus formed as the metal interface.

It is part of current prion science that copper plays a major role in the prion infectiveness. Recent German research has demonstrated that the healthy version of the Scrapie pathogen (believed to be PrP,sup.Sc) helps to maintain optimum concentration of copper in prion cell. Also that excess of manganese over copper is linked to a misfolding process that converts the copper regulating protein into the infective agent. (C Treiber et al, Biochemistry, 2006, DO11021/b060244h). N Robinson of University of Newcastle, UK, states "Copper is prone to bind tightly to the wrong proteins as Cu—PrP.". Clearly metals in steel alloys qualify as potential reactants to aberrant prion proteins.

There are two essential steps to removing prions from stainless steels and related ferrous metals. Firstly, to unfold the protein complex of the prion. This can be achieved by a number of clearly defined means including enzymes and both acid and alkaline chemicals. Thus far it appears that only chemicals very aggressive to metals will achieve the necessary unfolding (and probably decomposition) of such proteins. This has not yet been achieved with non-aggressive chemical products from current research.

The second means follows partial unfolding of the prion protein. This is followed by chelating the now more exposed di or trivalent metal to which the protein residue is firmly bound to the metal surface; likewise, to disentangle, disperse or dissolve remnants of partly unwound or disintegrated protein to a point where an appropriate chelating agent can react with the metal-protein complex binding the original prion to the surface. It is important to assure that any remnant protein is incapable of initiating infectivity by acting as a nucleus for enzymes of subsequent prion contact to reassemble structures capable of initiating infection.

This invention employs in part information in the author's U.S. Pat. No. 6,800,678 but adds several significant but novel improvements. Firstly, an alkalizing system yielding an operating pH at use dilution of from 11.5 to 13.3. This consists of a buffer system comprising a primary amine plus the mono valent metal salt of an hydroxyl organic acid having a molecular weight less than 220. Lithium salts are strongly preferred but potassium and sodium hydroxide and their alkaline salts may also be employed; though not as quickly reactive as those lithium.

The amine should possess the demonstrable property of reacting with proteins both to uncoil and solubilize proteins of the type found in prions, which are clearly defined in literature. The preferred amine is urea and its methyl and ethyl derivatives. Examples of other useful amines include methyl and ethylurea, ethanolamine, aminoethane, methylamine, ethylamine, propylamine, para toluidine, pyridine and tetra (2-hydroxypropyl)ethylaminediamine (Quadrol-BASF). Other structural arrangements of amines may also be expected to exercise similar behaviour but less effectively. Primary amines also contribute ammonium ions to the alkaline buffer system incorporated in this invention.

The organic acids useful in this invention include both saturated and unsaturated aliphatic and aromatic carboxylic acids and hydroxyl containing acids having a molecular weight of less than 135. The preferred acids are maleic acid, lactic acid, trifluroactetic acid and glycolic acids, each of which have previously been demonstrated by the author to provide useful solublizing or dispersing properties to structural components of biofilms.

For example, a novel acid mixture effective as a pre-soak for instruments on which biological residues have been allowed to dry before being subjected to proper reprocessing comprised typically:

| | |
|---|---|
| Glycolic acid | 7.5% wt/wt |
| Dodecylbenzene sulphonic acid | 2.5% wt/wt |
| Methyl dipropylene glycol (DPM) | 10.0% wt/wt |
| Pure water | Balance |

This is used as a 1 in 5 to 10 dilution with potable water; and is also capable of uncoiling and dispersing prion type proteins, which property is important where dried surgical residues have congealed and hardened on the surfaces of instruments before processing is possible.

The alkaline component of buffer systems employed in this invention is the mono valent inorganic alkali, with strong preference to lithium hydroxide, in the amount require to yield a pH at use dilution of from 12 to 13, preferably 12.0 to 12.7. Other alkaline salts of these mono valent metals may also be employed where found soluble in the total compositions envisaged. The amount required will be sufficient to yield a pH in a ready-to-use solution of from 11.5 to 13.3.

The second component is a unique, quite specialized chelating system, preferably of two or more components, that can effectively react with (chelate) the several di and trivalent metal ions found at pH 12 to 13 on the surface of the various alloys of steel used for the manufacture of surgical instruments. The metals involved may be either, but not limited to, iron, nickel, chromium, copper, manganese, zinc and tin. The appropriate chelating agents must be highly reactive at this high pH, each having a solubility constant (log K) at pH 1 2 above but not less that 15, preferably 20 or more to provide required reactivity to the wide range of metals likely to be encountered.

This latter requirement severely limits the choice of available agents to a chelating agent which reacts strongly with and breaks the strong internal bonding between the metal ion and its receptor group on the terminal end of the protein coil. This constitutes a novel application for chelating agents which are normally intended to react with metal ion already in solution or those readily solubilised into aqueous solution at an appropriate pH.

Of similar novelty is the structural configuration of the chelating agent to be used in a mixed reactive system. Two chelating agents are chosen, each having quite different spatial structures in alkaline aqueous solution, giving the widest possible chance of reacting with a wide range of complex structures formed with di and trivalent ions strongly bound below and within and on the protein coils of prions; after being partially or totally uncoiled by other ingredients in the intended products. A typical preferred mix of chelating agents to yield this element of reactivity is that of sodium heptagluconate and diethylene triamine pentaacetic acid (DPTA).

Desired chelating agents are those belonging to the groups of substituted di and triethylamines and di isopropylamine; reactant products of phosphonic acids known commercially as "phosphonates"; derivatives of nitrilotriacetic acid and glycine; derivatives of gluconic acid and like structures that are also highly reactive under the disclosed conditions. No doubt other chelating agents may contribute to the defined objective outlined and are therefore included in this specification.

The amount of chelating agent will range from 0.01 percent in ready-to-use formulations to 15.0 percent by weight.

The third component constitutes an efficient biofilm removal system which is an essential requirement of this invention. The surfactant system to be incorporated will be that of the author's Australian Patent 2001275599 and U.S. Pat. No. 6,885,678, appropriately modified to control the extreme tendency to foaming in high pressure endoscope washing machines due to the combination of ingredients employed in final formulations. This comprises a mixture of surfactants, polar solvents, and a nitrogen containing biocide.

This system will comprise at least one surfactant in the range 0.05 to 15 percent by weight; at least one polar solvent with a molecular weight of less than 160; and at least one nitrogen containing biocide in the total amount of 0.5 to 15 percent by weight.

The one or more nitrogen biocides will be selected from an alkyl (C8-14) dimethylbenzyl ammonium halide; a dialkyl (C4-10) or trimethyl benzyl or ethylbenzyl ammonium halide; an alkyl (C10-18) amine halide; benzethonium chloride (Hyamine 1622); cetyl pyrimidum bromide; chlorhexidine digluconate, diacetate and other derivative thereof; dodecylamine hydrochloride; dimethyl dodecylamine halide or gluconate; methylbisthiocyanate; tetrachloro isonaphthalnitrile; 2-bromo-2-nitro-1,3 propanol; 5-chloro-4-isothiazolin; and 2-methyl-4-isothiazolin-3 one.

The surfactant system will comprise at least one surfactant selected from an alkyl polysaccharide; a non-ionic surfactant; an alkyl aryl amine surfactant; a poly ethoxylate of an alkylamine; a halogen terminated alkyl (C8-18) polyethoxylate; and an alkyl (C8-18) betaine.

The solvent will be selected from one of more C 1-9 alcohol and hydroxyacid esters esters; ether; ketone; mono and poly ethylene and propylene glycols and their methyl, ethyl propyl and butyl esters and ethers; aromatic alcohols; cyclic nitrogen solvents containing 8 or less carbon atoms; pyridine, pyrrolidone and methyl pyrrolidone; in which the solvent comprises from about 1 to 20 percent by weight of a ready-to-use formulation or from 10 to 80 percent by weight of a dilutable concentrate.

The fourth major improvement is the addition of a biostatic passivating (antioxidant) agent to these formulations. Its dual purpose is firstly to passivate metals freshly deoxidised by the chelating processes envisaged. Secondly, to leave freshly decontaminated surfaces in a condition that will prevent or seriously ameliorate future binding of prions to potentially reactive metals; and either corrosion or discoloration emanating from hard water components.

Such an ingredient is found in the group of organo-functional silanes. Alkoxy amino functional silanes are well recognized as valuable agents for corrosion resistance, adhesion promotion, providing cross linking for surface coatings, as drying agents for metals and as pre-polymer end-cappers. Amino functional silanes are particularly useful as metal corrosion inhibitors being applied thereto by various common application procedures; having the property of coating then, by subsequent hydrolysis to silanols, reacting with metal surfaces. The silane, either within aqueous solution and/or prior to or subsequent to deposition, can be readily hydrolysed on the surface by water, alcohols and alkaline solutions yielding silanol films firmly bound by hydrophobic covalently linked bonding; thus providing useful term corrosion protection for commercial metals. This normally requires immersing metals in an aqueous or alcoholic aqueous solution at a concentration of 2 to 5 percent by weight silane, then drying, preferably baking, to yield a permanent protective film. Where such films are used on metal requiring painting it is advisable to deposit a second silane film, usually of a simpler silane composition, to act as a coupling agent between the initial silane film and paint (U.S. Pat. Nos. 5,750,391 and 6,261,638). The former is a multi-functional silane whereas the latter is a mono-functional silane.

The hydrolysed residue of mono functional alkoxyamino silanes on metals, in particular 3-aminopropyl trimethoxy silane, has been extensively studied and reported as being non-toxic, colourless, odourless and strongly persistent in the atmosphere. It therefore poses no hazard when retained at molecular level layers on surgical instruments.

Using the principles of the author's Australian Patent 46948/97 and U.S. Pat. No. 6,525,101, it is possible to incorporate an amino functional silane into the aqueous alkaline compositions of the present invention. By this means, silane is deposited on metal as it is cleaned in its original structure, ie 3-aminopropyl triethoxysilane. While other cleaning actions are occurring within a solution the silane progressively hydrolyses within the aqueous solution, shedding three molecules of methanol; the hydrolysed silanol now becomes firmly bound to metal surfaces.

Silanes demonstrating this potential behaviour are glycidopropyl trimethoxysilane; y-amino propyl(trimethoxy)silane; y-methacrylpropyl(trimethoxy)silane; N-((2-vinylbenxylamino(ethyl))-3-aminopropyl(trimethoxy)silane; ethyl 3-aminopropyl(trimethyl)silane; 3-aminopropyl(trimethoxy)silane being preferred because of its more favourably reactivity in alkaline solutions. The amount incorporated in a formulation is from 0.01 to 5.0 percent by weight in the final products.

Residual silane left on the surface of instruments serves as an anti-oxidant by passivating newly washed metal, preventing the now prevalent oxidation discolouration of stainless steel that occurs routinely following cleaning with heated conventional alkaline detergents; thus preserving the shiny appearance of instruments, as well as obviating spotting corrosion from dried water minerals, particularly salt.

The major difference in use of an amino functional in this application is its use in a fully hydrolyzed (silanol) condition at low concentration to passivate rather than coat metal. Concentrations as low as 0.005 percent by weight in aqueous solution will passivate some highly corrosive metals when wet. Passivation is intended to prevent rapid discoloration or reactions occurring on the surface of stainless steels and similar metals immediately after alkaline chemical reprocessing.

Progressive discolouration of reprocessed surgical instruments after routine alkaline in centralized sterile cleaning sections of health facilities is a major and costly problem that can be largely if not totally eliminated in this simple inexpensive manner.

While a silane employed in this invention is part of a detergent concentrate, it is only under the most exceptional of circumstances that the 3-aminopropyl trimethoxylsilane can be incorporated separately into an alkaline detergent system, eg as Part A of example formulation; alternatively it may be fed into alkaline detergent solutions by means of an electronically controlled feeder; even as a last resort in particular reprocessing machinery directly into rinse water by similar means.

In either case the silane will be quickly hydrolysed by alkali retained on wet metal surfaces, the optimum reaction rate occurring at pH 10.0-10.5. Hydrolysis is quite fast particularly at elevated temperatures, ie 50-60° Celsius, under which condition the intended formulations are designed to operate.

A particular advantage derived from the silane is that the hydrolysed silanol version is firmly and/or semi-permanently covalently bound to stainless and ferrous metals as well as aluminium and zinc metal surfaces, providing semi-permanent surface oxidation resistance due to reaction between silanol and the most reactive sites on the surface of metal.

This phenomenon will serve to greatly reduce the opportunity of binding by prions to potentially reactive sites on the surface of crystals of reprocessed stainless steels which, theory has it, are the sites where prion proteins react most strongly; and from which they are most difficult to remove chemically.

This latter objective will be highly advantageous to facilitate removal of surgical residues contaminated with prions; and, most importantly, to assure the decontamination of surgical instruments and related equipment in common processing machinery found in Central Sterile Departments of hospitals, quickly and at low cost.

This process has particular practical advantages where available water supply is hard or brackish, as is frequently the case in country areas; specially in isolated settlements where field medicine is practiced. This process negates the troublesome problem of extensive spotting from dried water residues, which induces surface corrosion of instruments and surfaces, shortening the life of very expensive instruments and surfaces.

The truly unique factor is the method of formulating aminosilanes to produce solutions having compositions wherein the aminosilane remains chemically stable in a quite alkaline environment—until it is required in practice and is then diluted with water for use. This is achieved by creating a "non-aqueous" solution containing at least 20 percent by weight of water (required initially to solubilise other ingredients) in triethyleneglycol. This latter phenomenon also occurs at varying rates with some alcohols and other polyglycols and their derivatives.

As was demonstrated in my Australian Patent 46848/97, triethyleneglycol reacts exothermally with water to form a dehydrate; in this case consuming (reacting with) all of the free water in the solution, thereby eliminating the possibility of aqueous ionic reactions that may cause unwanted reactions between components.

EXAMPLE

A typical concentrated formulation to be diluted immediately prior to use is as follows:

| Part 1 | Demineralised water | 20.0 g |
| | Triethylene glycol | 20.0 g |
| | Urea | 4.5 g |
| | Alkyl glucocide surfactant | 2.3 g |
| | Teric 9A5 (Orica) | 1.75 g |
| | Dodecylamine hydrobromide | 0.27 g |
| | Lactic acid | 0.8 g |
| | DTPA (100%) | 3.0 g |
| | Sodium heptagluconate | 3.5 g |
| | Lithium hydroxide | 0.25 g |
| | pH adjust to 13.0 | |
| Part 2 | Add: | |
| | Triethyleneglycol | 42.13 |
| | Slowly add with stirring | |
| | 3-aminopropyltrimethoxysilane | 1.5 g |
| Part 3 | Slowly add Part 2 into Part 1 with constant stirring. | |
| | TOTAL | 100.0 gram |

(DTPA refers to Diethylenetriamine pentaacetic acid)

This concentrated product would be diluted from 1 part to 5 parts of water to 1 part to 25 parts of water and used at temperatures from 20 to 60° Celsius.

The initial cleaning operation would be followed by a water rinse at the same temperature lasting at least 3 minutes to ensure complete hydrolysis of the alkoxy aminosilane on the surface of cleaned articles.

Throughout the description and claims of this specification, the word "comprise" and variations of the word, such as "comprising" and "comprises," are not intended to exclude other additives, components, integers or steps.

The invention claimed is:

1. A cleaning composition comprising:
   (i) 0.1 to 10 percent by weight of the cleaning composition of a biofilm-removing detergent solution comprising a combination of an alkyl (C8-18) polysaccharide, a non-ionic surfactant and a nitrogen containing surfactant-biocide;
   (ii) 2 to 80 percent by weight of the cleaning composition of one or more polar solvent selected from the group consisting of a primary or secondary alcohol, an ester, an ether, a ketone, a glycol, an aromatic alcohol, and a cyclic nitrogen solvent containing 8 or less carbon atoms;
   (iii) 0.5 to 15 percent by weight of the cleaning composition of one or more amines selected from the group consisting of urea, methyl and ethyl urea, aminomethane, alkylamines containing 1 to 4 carbon atoms, pyridine, paratoludine, and tetra (2-hydroxypropyl) ethylene diamine;
   (iv) two or more chelating agents selected from the group consisting of a substituted di and tri ethylamine, derivatives of phosphonic acid and its substituted derivatives, derivatives of nitrilotriacetic acid, derivatives of gluconic acid, glycine and derivatives thereof;
   (v) 0.1 to 5.0 percent by weight of the cleaning composition of an alkaline buffer system providing a pH of about 11.5 to 13.3 in aqueous solution, comprising low molecular weight organic and/or hydroxyl organic acids containing 7 or less carbon atoms, and a mono valent alkali metal hydroxide; and
   (vi) 0.005 to 5.0 percent by weight of the cleaning composition of an organofunctional silane.

2. A cleaning composition according to claim 1 wherein the chelating agents have a solubility coefficient (Log K) in excess of 15 with metals found in stainless steel type medical instruments.

3. A cleaning composition according to claim 2 wherein said two or more chelating agents each have a distinct spatial configuration to one another in solution with a pH in excess of 11.

4. A cleaning composition according to claim 1 wherein the monovalent alkali metal hydroxide is selected from the group consisting of lithium, sodium and potassium hydroxide.

5. A cleaning composition according to claim 1 wherein the organofunctional silane is selected from the group consisting of glycidopropyl trimethoxysilane; y-amino propyl trimethoxy silane, y-methacrylpropyl (trimethoxy) silane, N-((2-vinylbenzylamino (ethyl)-3-aminopropyl trimethoxy silane, and ethyl 3-aminopropyltrimethyl silane.

6. A cleaning composition according to claim 5 wherein the organofunctional silane is y-aminopropyl trimethoxysilane.

7. A cleaning composition according to claim 1 wherein said biofilm removing detergent system comprises a multi-component surfactant system wherein at least one surfactant is selected from the group consisting of an alkyl polysaccharide surfactant containing from 8 to 18 carbon atoms; a non-ionic surfactant containing from 8 to 28 carbon atoms and/or from 4 to 12 moles of ethylene oxide; an amine oxide containing from 12 to 18 carbon atoms; an ethoxylated alkyl amine containing from 10 to 16 carbon atoms and 1 to 8 moles of ethylene oxide; a halide capped alkyl containing from 8 to 18 carbon atoms and from 4 to 10 moles of ethylene oxide; an alkyl (C8-14) dimethylbenzyl amine halide; lauric mono- di- or triethanolamine; a nitrogen containing biocide selected from alkyl (C8-14) benzyl ammonium halide; a dialkyl (C4-10) di or tri methylbenzyl or ethylbenzyl ammonium halide; an alkyl (C10-20) amine halide; benzethonium chloride; cetyl pyrimidum halide; chlorhexidine gluconate, acetate or other derivative; dimethyl dodecylamine halide or gluconate; methylbis thiocyanate;
   tetrachloroiso naphthalonitrile; 2-bromo-2-nitro-1,3propanol; 5-chloro-4-isothiazolin and 2-methyl-4-isothiazolin-3-one.

8. A cleaning composition according to claim 7 wherein said surfactant is present in the amount of from 0.05 to 15 percent by weight of the biofilm removing detergent system.

9. A cleaning composition according to claim 1 wherein the low molecular weight hydroxyl organic acid of the alkaline buffer system comprises from 0 to 3 hydroxyl groups.

10. A cleaning composition according to claim 9 wherein the alkaline buffer system is present in an amount of 0.5 to 5.0 percent by weight of the cleaning composition and said polar solvent is present in an amount of 5 to 80 percent by weight of the cleaning composition.

11. A cleaning composition according to claim 1 wherein said alkylamine is selected from the group consisting of methylamine, ethylamine and propylamine.

12. A cleaning composition according to claim 1 wherein the chelating agents are present in a total amount of 0.1 to 15 percent by weight of the cleaning composition.

13. A cleaning composition according to claim 12 wherein one of the chelating agents is a heptagluconate.

14. A cleaning composition according to clam 1 wherein the organofunctional silane is present in an amount of 0.1 to 5.0 percent by weight of the cleaning composition.

15. A cleaning composition according to claim 1 wherein said organofunctional silane is added to a detergent solution first formed by mixing said parts (i) to (v).

16. A cleaning composition according to claim 15 wherein said organofunctional silane is added either manually or by electronically controlled injection equipment into washing equipment containing said detergent solution or into rinse water after cleaning with said detergent solution.

17. A cleaning composition of claim 1 diluted prior to use, 1 part cleaning composition: 5 to 100 parts water or a low molecular weight alcohol.

18. A cleaning composition according to claim 17, wherein said alcohol is ethanol.

19. A process of cleaning, decontaminating and/or passivating metallic surgical instruments and/or equipment, by hand or machine processing, which process comprises applying to said instruments and/or equipment a cleaning composition according to claim 1.

20. A process of cleaning instruments or processing machines by contacting said instruments or processing machines with a composition according to claim 1 at a temperature from 20° C. to 60° C., wherein said machines include a water rinse cycle at the same temperature or hotter.

* * * * *